(12) United States Patent
Fukada et al.

(10) Patent No.: US 10,493,116 B2
(45) Date of Patent: Dec. 3, 2019

(54) LONGEVITY GENE EXPRESSION ENHANCER

(71) Applicant: Shiseido Company, Ltd., Chuo-ku, Tokyo (JP)

(72) Inventors: Kaedeko Fukada, Yokohama (JP); Tatsuya Hasegawa, Yokohama (JP); Hiroshi Mori, Yokohama (JP); Yoshiharu Suzuki, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 16/054,001

(22) Filed: Aug. 3, 2018

(65) Prior Publication Data

US 2018/0344791 A1   Dec. 6, 2018

Related U.S. Application Data

(63) Continuation of application No. 15/500,687, filed as application No. PCT/JP2015/071679 on Jul. 30, 2015.

(30) Foreign Application Priority Data

Aug. 1, 2014   (JP) .................................. 2014-158163

(51) Int. Cl.
  *A61K 36/23* (2006.01)
(52) U.S. Cl.
  CPC .......... *A61K 36/23* (2013.01); *A61K 2236/15* (2013.01); *A61K 2236/17* (2013.01); *A61K 2236/333* (2013.01); *A61K 2236/53* (2013.01)
(58) Field of Classification Search
  CPC ................ A61K 36/23; A61K 2236/15; A61K 2236/17; A61K 2236/333; A61K 2236/53
  See application file for complete search history.

(56) References Cited

U.S. PATENT DOCUMENTS

| 2011/0020477 | A1* | 1/2011 | Iriyama | A61K 8/4946 424/733 |
|---|---|---|---|---|
| 2011/0070258 | A1 | 3/2011 | Jiminez del Rio et al. | |
| 2011/0318284 | A1 | 12/2011 | Dal Farra et al. | |
| 2014/0037762 | A1 | 2/2014 | Maeda et al. | |

FOREIGN PATENT DOCUMENTS

| EP | 2389922 A1 | 11/2011 |
|---|---|---|
| EP | 2676670 A1 | 12/2013 |
| JP | 2003-026694 A | 1/2003 |
| JP | 2004-026697 A | 1/2004 |
| JP | 2013-112636 A | 6/2013 |
| JP | 2013-203670 A | 10/2013 |
| JP | 5666053 B1 | 12/2014 |
| WO | WO 2012/111643 A1 | 8/2012 |

OTHER PUBLICATIONS

Nukitrangsan N; Okabe T; Toda T; Inafuku M "Effect of Peucedanum japonicum Thunb Extract on High-fat Diet-induced Obesity and Gene Expression in Mice" J. Oleo Sci. 61, (2) 89-101 (2012) (Year: 2012).*

Hisamoto et al., "Antioxidant Compounds from the Leaves of *Peucedanum japonicum* Thunb," Journal of Agricultural and Food Chemistry, Aug. 1, 2003, 51(18):5255-5261.

Lavu et al., "Sirtuins—novel therapeutic targets to treat age-associated diseases," Nature Reviews, Drug Discovery, Oct. 1 2008, 7(10):841-853 and one page corrigendum.

Maeda, Goki, "Studies on antioxidant activities of Okinawan vegetables and those antioxidant substances," Okinawa Prefectural Agricultural Research Center Kenkyu Hokoku, 2009, 2:1-29.

Morioka et al,. "The modifying effect of *Peucedanum japonicum*, a herb in the Ryukyu Islands, on azoxymethane-induced colon preneoplastic lesions in male F344 rats," Cancer Letters, Mar. 18, 2004, 205(2):133-141.

Nukitrangsan et al. "Effect of *Peucedanum japonicum* Thunb. Extract on High-fat Diet-induced Obesity and Gene Expression in Mice," J. Oleo Sci., 2012, 61(2):89-101.

Onogi, Hiroshi, "Anti-atherosclerotic and vasorelaxant effects of Peucedanum japonicum on Yaku Island," Food Processing and Ingredients, 2009, 44(12):38-40.

Su et al., "Rutin, a Flavonoid and Principal Component of *Saussurea involucrata*, Attenuates Physical Fatigue in a Forced Swimming Mouse Model," International Journal of Medical Sciences, Mar. 29, 2014, 11(5):528-537.

Sun et al. "Anti-Aging Effects of Hesperidin on *Saccharomyces cerevisiae* via Inhibition of Reactive Oxygen Species and UTH1 Gene Expression," Biosci. Biotechnol. Biochem., Apr. 7, 2012, 76(4):640-645.

Tamura-Norimatsu et al., "Anti-edema Effect of a Drink Containing Peucedanum Japonicum Thunb. in Healthy Japanese Women," Database Biosis [Online] Biosciences Information Service, 2012, Database accession No. PREV201200771073, abstract.

de Boer et al., "SIRT1 stimulation by polyphenols is affected by their stability and metabolism," Mechanisms of Ageing and Development, Jul. 1, 2006, 127(7):618-627.

Hubbard et al., "Small molecule SIRT1 activators for the treatment of aging and age-related diseases," Trends in Pharmacological Sciences, Mar. 2014, 35(3):146-154.

Pallauf et al., "Nutrition and Healthy Ageing: Calorie Restriction or Polyphenyl-Rich 'MeditarrAsian' Diet?", Oxidative Medicine and Cellular Longevity, 2013, Article 707421, 14 pages.

(Continued)

*Primary Examiner* — Aaron J Kosar
(74) *Attorney, Agent, or Firm* — Foley & Lardner LLP

(57) ABSTRACT

The present invention provides a novel sirtuin-1 activating agent, and a formulation for suppressing cell senescence caused by oxidative stress, comprising the agent.

In particular, the invention provides a sirtuin-1 activating agent consisting of a plant body or solvent extract of *Peucedanum japonicum* Thunb., and a formulation for suppressing cell senescence due to oxidative stress, comprising the agent.

6 Claims, 2 Drawing Sheets

(56) References Cited

OTHER PUBLICATIONS

Suda et al., "Polyphenol Contents and Radical-Scavenging Activity of Extracts from Fruits and Vegetables in Cultivated in Okinawa, Japan," Nippon Shokuhin Kagaku Kogaku Kaisha, 2005, 52(10):462-471, with English abstract on first page.

Haenold et al,. "Oxidative damage, aging and anti-aging strategies," AGE: Journal of the American Aging Assocation, Sep. 1, 2005, 27(3):182-199.

\* cited by examiner

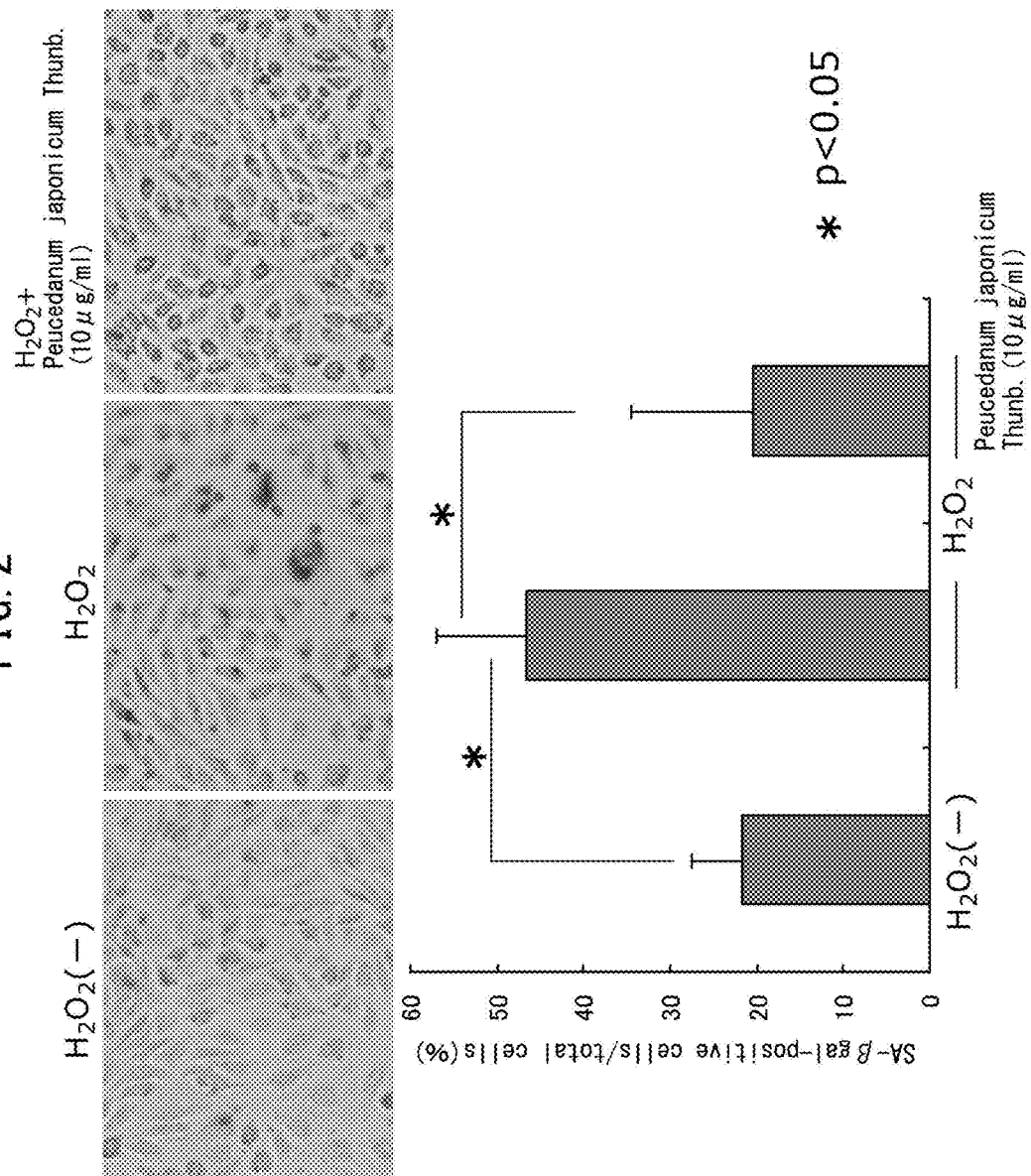

LONGEVITY GENE EXPRESSION ENHANCER

CROSS-REFERENCE TO RELATED APPLICATIONS

This application is a Continuation of U.S. application Ser. No. 15/500,687, which is the U.S. National Stage application of PCT/JP2015/071679, filed Jul. 30, 2015, which claims priority from Japanese application JP 2014-158163, filed Aug. 1, 2014.

TECHNICAL FIELD

The present invention provides a sirtuin-1 activating agent, and a formulation for suppressing cell senescence caused by oxidative stress, that contains the agent.

BACKGROUND ART

Much attention had been directed in recent years toward genes for $NAD^+$-dependent deacetylases known as sirtuins, as longevity genes. The Sir2 gene was first identified in yeast, and in experimental systems using lower animals such as yeast and nematodes, it has been reported that lifespan is shortened by deletion of Sir2, while lifespan is lengthened when it is overexpressed (NPLs 1 and 2). The Sir2 gene is conserved in mammals, with sirtuin-1 to sirtuin-7 having been identified. Much attention among these has been focused on sirtuin-1, as it is the one with a structure and function most resembling yeast Sir2.

The protein target of sirtuin-1 has been identified, and research suggests that it is involved in intracellular metabolism, energy consumption, and inflammation and stress response pathways. In addition, activation of the sirtuin-1 gene is thought to have effects for arteriosclerosis, diabetes, heart disease, cancer, diabetes complications, neuropathic pain, microvascular dysfunction, life extension, mitochondrial disease, mitochondrial myopathy, neurodegenerative diseases (such as Alzheimer's disease, amyotrophic lateral sclerosis and Parkinson's disease), chronic obstructive pulmonary disease (COPD) and psoriasis (NPLs 3 and 4).

Among sirtuin activating substances there are known polyphenol compounds, which include resveratrol found in grape peels and the like or fisetin found in strawberries and apples, and non-polyphenol compounds such as SRT1720. The major pharmaceutical company GlaxoSmithKline plc of England is vigorously conducting development of sirtuin-1 activating substances, and for example, SRT2104 which has been reported to be effective for prevention of type 2 diabetes, osteoporosis, sarcopenia and skeletal muscle atrophy (Reference 5) is currently in the clinical trial stage.

In addition, it is known that *Peucedanum japonicum* Thunb. plant body and its extract has action of inhibiting disaccharidase and efficacy for prevention and treatment of diabetes as well as countering obesity (PTL 1), has a cell-activating effect, antioxidant effect and melanin production inhibiting effect (PTL 2), exhibits inhibitory action against heparanase activity and is effective for preventing and improving wrinkles (PTL 3), and promotes ceramide synthesis (PTL 4).

*Peucedanum japonicum* Thunb., also known as "longevity grass", is a plant of which it has been traditionally said in Okinawa Prefecture, that "eating one serving extends the life by a day". Sirtuin genes have already been known as longevity genes for over 15 years. However, absolutely no previous reports exist regarding whether the plant body or extract of *Peucedanum japonicum* Thunb. has a sirtuin-1 activating effect, and finding the connection between these has not been an easy task. Since traditional accounts regarding *Peucedanum japonicum* Thunb. and longevity do not constitute scientific evidence, it has not been easy to establish a connection between them.

CITATION LIST

Patent Literature

[PTL 1] Japanese Unexamined Patent Publication No. 2003-26694
[PTL 2] Japanese Unexamined Patent Publication No. 2004-26697
[PTL 3] International Patent Publication No. WO2009/123215
[PTL 4] Japanese Unexamined Patent Publication No. 2005-194239

Non-Patent Literature

[NPL 1] Genes Dev., 13(19): 2570-80 (1999)
[NPL 2] Nature, 410(6825): 227-30 (2001)
[NPL 3] Nat. Rev. Drug Discov., 7(10): 841-853 (2008)
[NPL 4] J. Invest. Dermatol., 129(1): 41-49 (2009)
[NPL 5] Aging. Cell, 13(5): 787-796 (2014)
[NPL 6] Proc. Natl. Acad. Sci. USA, 92(20): 9363-9367 (1995)
[NPL 7] Nat. Protoc., 4(12): 1798-1806 (2009)
[NPL 8] J. Atheroscler. Thromb., 17(9): 970-979 (2010)
[NPL 9] J. Atheroscler. Thromb. Vasc. Biol., 30(11): 2205-2211 (2010)

DISCLOSURE OF THE INVENTION

Problems to be Solved by the Invention

It is an object of the present invention to provide a sirtuin-1 activating agent, and a formulation for suppressing cell senescence caused by oxidative stress, that contains the agent.

Means for Solving the Problems

As a result of much diligent research, the present inventors have found that the plant body and solvent extract of *Peucedanum japonicum* Thunb. (also known as "longevity grass") function as sirtuin-1 activating agents, and have thereupon completed the following invention.

(1) A sirtuin-1 activating agent consisting of a plant body or solvent extract of *Peucedanum japonicum* Thunb.
(2) The sirtuin-1 activating agent according to (1), wherein the solvent extract is a water-containing ethanol extract.
(3) The sirtuin-1 activating agent according to (1) or (2), wherein the plant body of *Peucedanum japonicum* Thunb. is the leaves, stem or entire plant.
(4) A formulation for suppressing cell senescence due to oxidative stress, comprising a sirtuin-1 activating agent consisting of a plant body or solvent extract of *Peucedanum japonicum* Thunb.
(5) The formulation according to (4), wherein the solvent extract is a water-containing ethanol extract.
(6) The formulation according to (4) or (5), wherein the plant body of *Peucedanum japonicum* Thunb. is the leaves, stem or entire plant.

(7) The formulation according to any one of (4) to (6), wherein the formulation is an ingestion formulation.

(8) A plant body or solvent extract of *Peucedanum japonicum* Thunb., for suppression of cell senescence due to oxidative stress.

(9) The plant body or solvent extract of *Peucedanum japonicum* Thunb. according to (8), wherein the solvent extract is a water-containing ethanol extract.

(10) The plant body or solvent extract of *Peucedanum japonicum* Thunb. according to (8) or (9), wherein the plant body of *Peucedanum japonicum* Thunb. is the leaves, stem or entire plant.

(11) Use of a sirtuin-1 activating agent for production of a formulation for suppressing cell senescence due to oxidative stress, wherein the sirtuin-1 activating agent comprises a plant body or solvent extract of *Peucedanum japonicum* Thunb.

(12) The use according to (11), wherein the solvent extract is a water-containing ethanol extract.

(13) The use according to (11) or (12), wherein the plant body of *Peucedanum japonicum* Thunb. is the leaves, stem or entire plant.

(14) The use according to any one of (11) to (13), wherein the formulation is an ingestion formulation.

(15) A method for suppressing cell senescence due to oxidative stress, wherein a sirtuin-1 activating agent consisting of a plant body or solvent extract of *Peucedanum japonicum* Thunb. is administered to a subject in need of suppression of cell senescence due to oxidative stress.

(16) The method according to (15), wherein the solvent extract is a water-containing ethanol extract.

(17) The method according to (15) or (16), wherein the plant body of *Peucedanum japonicum* Thunb. is the leaves, stem or entire plant.

(18) The method according to any one of (15) to (17), wherein the sirtuin-1 activating agent is orally administered.

(19) A method for prevention or treatment of a disease selected from among anti-arteriosclerosis, anti-diabetes, heart disease, anti-cancer, diabetes complications, neuropathic pain, microvascular dysfunction, life extension, mitochondrial disease, mitochondrial myopathy, neurodegenerative disease (such as Alzheimer's disease, amyotrophic lateral sclerosis or Parkinson's disease), chronic obstructive pulmonary disease, (COPD) and psoriasis, wherein a sirtuin-1 activating agent consisting of a plant body or solvent extract of *Peucedanum japonicum* Thunb. is administered to a subject in need of treatment for such a disease.

(20) The method according to (19), wherein the solvent extract is a water-containing ethanol extract.

(21) The method according to (19) or (20), wherein the plant body of *Peucedanum japonicum* Thunb. is the leaves, stem or entire plant.

(22) The method according to any one of (19) to (21), wherein the sirtuin-1 activating agent is orally administered.

Effect of the Invention

Administration of a sirtuin-1 activating agent of the invention is able to activate sirtuin-1. According to the invention it is possible to provide an ingestion formulation containing a sirtuin-1 activating agent.

BRIEF DESCRIPTION OF THE DRAWINGS

FIG. 2 shows the cell senescence-inhibiting effect of *Peucedanum japonicum* Thunb. against oxidative stress.

BEST MODE FOR CARRYING OUT THE INVENTION

Figure 1:
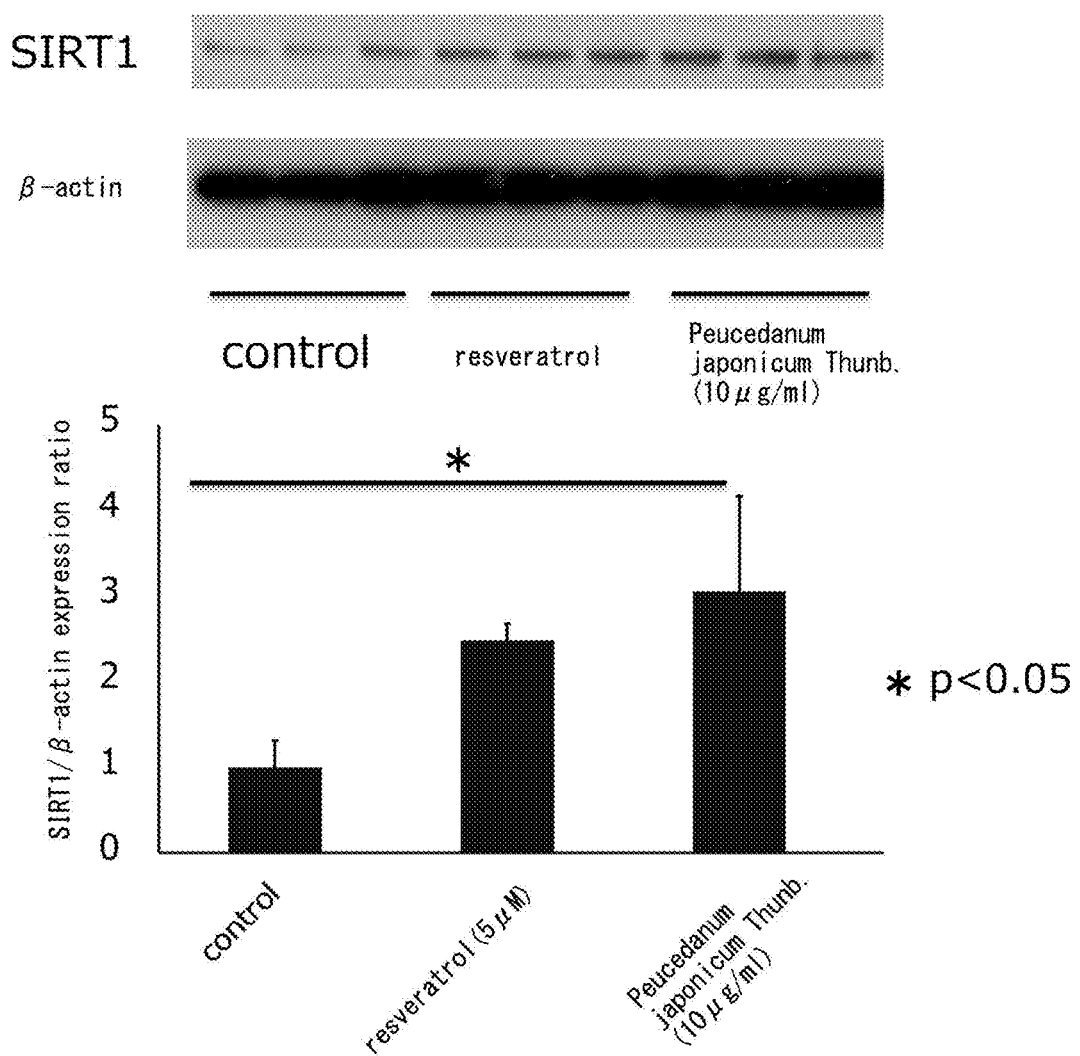
FIG. 1 shows evaluation of Western blotting of sirtuin-1 expression.

Administration of a sirtuin-1 activating agent of the invention is able to activate sirtuin-1.

Cell senescence due to oxidative stress can be suppressed by activation of the sirtuin-1 gene. Cell senescence due to oxidative stress means damage to intracellular proteins, lipids, DNA and the like caused by peroxides and free radicals produced by oxidative stress including exposure to chemical agents produced by smoking, excessive eating or drinking or active oxygen generation, overfatigue, or exposure to ultraviolet rays or radiation, whereby an irreversible condition results in which cell replication is halted or proliferation becomes impossible, and it is distinguished from the phenomenon of senescence due to reduced cell proliferation activity as occurs with aging. Evaluation of cell senescence is routinely carried out in the field, with available senescence markers including cell senescence-associated β-galactosidase (SA β-Gal) (NPLs 6 and 7). The sirtuin-1 gene is known to be associated with cell senescence due to oxidative stress, and for example, it has been reported that resveratrol and statins can activate the sirtuin-1 gene and suppress cell senescence due to oxidative stress (NPLs 8 and 9). Activation of the sirtuin-1 gene is therefore useful for suppression of cell senescence due to oxidative stress.

Activation of the sirtuin-1 gene is thought to be useful for prevention or treatment of anti-arteriosclerosis, anti-diabetes, heart disease, anti-cancer, diabetes complications, neuropathic pain, microvascular dysfunction, life extension, mitochondrial disease, mitochondrial myopathy, neurodegenerative diseases (such as Alzheimer's disease, amyotrophic lateral sclerosis and Parkinson's disease), chronic obstructive pulmonary disease (COPD) and psoriasis.

Sirtuin-1 gene activation, according to the invention, means promoted expression of the sirtuin-1 gene, and for example, it means promoted sirtuin-1 gene expression when a sirtuin-1 activating agent has been administered, compared to a non-administered state (control), with a statistically significant difference where the significance level is 5% (by Student's t test, for example). Also, activation of the sirtuin-1 gene, according to the invention, may mean that when a sirtuin-1 activating agent has been administered, the sirtuin-1 gene expression is promoted by, for example, 10% or more, 20% or more, 30% or more, 40% or more, 50% or more, 60% or more, 70% or more, 80% or more, 90% or more, 100% or more, 200% or more, 300% or more, 400% or more or 500% or more, compared to a non-administered state (control).

The sirtuin-1 activating agent of the invention contains an orally ingestible extract of *Peucedanum japonicum* Thunb. as an active ingredient.

The *Peucedanum japonicum* Thunb. (alternate name: "longevity grass") to be used for the invention is a plant of Umbelliferae *Peucedanum* L. which is distributed throughout Ishikawa Prefecture, west of the Kanto region (Honshu island), Shikoku, Kyushu, Okinawa and the Korean peninsula, China, Taiwan and the Philippines, and is a perennial herb that grows in well sunlit seashore areas (Newly Revised Makino's Color Illustrated Compendium of Oriental Drugs, p. 368 (2002)).

*Peucedanum japonicum* Thunb. may be used either in raw or dried form, but it is preferably used as a dry powder or extract from the viewpoint of ease of use and formulation.

The method for obtaining dry powder may be shredding and pulverizing of the entire plant or parts thereof (leaves, flowers, roots, etc.), followed by drying, or shredding or pulverizing of the dried plant to obtain a dry powder. Another method that may be employed is shredding and pulverization of the plant, followed by fermentation or enzyme treatment, and then drying and pulverizing to the desired particle size, as necessary.

The extraction method for the extract to be used for the invention may be solvent extraction. For solvent extraction, the entire plant or a portion thereof (leaves, flowers, roots, etc.) are dried, if necessary, further shredded and crushed if necessary, and then extracted using an aqueous extraction agent such as cold water, warm water or hot water at the boiling point or lower or a water-containing organic solvent, or an organic solvent such as methanol, ethanol, 1,3-butanediol or ether, at ordinary temperature or with heating. However, the extraction process is not limited to solvent extraction and may be carried out by any ordinary method known in the field. The form of the extract does not have to be the extract itself, as it may be in a form obtained by appropriate dilution or concentration by an ordinary method, or a powder or solid mass obtained by drying the extract.

The extraction solvent to be used for the invention is preferably a water-containing organic solvent, particularly preferably it is selected from among water-containing lower alcohols such as water-containing methanol, water-containing ethanol or water-containing 1,3-butanediol, and it is most preferably water-containing ethanol. The water content in this case may be 20 to 80 mass %, for example.

The sirtuin-1 activating agent of the invention may be administered by ingestion or topical application, but it is preferably ingested.

When a sirtuin-1 activating agent of the invention is to be ingested, the content of the Peucedanum japonicum Thunb. plant body or its solvent extract may be appropriately determined depending on the type of plant, the purpose, the form and the method of use. It is preferably prepared so that the amount of plant body or solvent extract consumed per day per adult is about 0.16 g to about 16 g (as dry mass). It is more preferably prepared to about 0.8 to about 8 g (as dry mass). When it is to be utilized as an ingestion formulation, the active ingredient of the invention is preferably added in an amount allowing the sirtuin-1 activating effect to be satisfactorily exhibited.

When the sirtuin-1 activating agent of the invention is to be added to an ingestion formulation, it may be used in combination with desired additives selected as necessary. Excipients or the like may be added as additives.

Excipients may be any that are commonly used when preparing desired dosage forms, and examples include starches such as wheat starch, rice starch, corn starch, potato starch, dextrin, cyclodextrin and the like, crystalline celluloses, saccharides such as lactose, glucose, sugar, reduced maltose, rice jelly, fructooligosaccharides or emulsified oligosaccharides, and sugar alcohols such as sorbitol, erythritol, xylitol, lactitol and mannitol. Any of these excipients may be used alone or in combinations of two or more.

Other publicly known coloring agents, preservatives, thickeners, binders, disintegrators, dispersing agents, stabilizers, gelling agents, antioxidants, surfactants, preservatives, pH regulators or the like may also be selected for use as appropriate.

The ingestion form may be selected as an appropriate form, such as liquid, solid, granular, particulate, paste or gel form.

EXAMPLES

The present invention will now be explained in greater detail by examples. However, the invention is in no way limited by the examples.

Experiment 1: Preparation of Sample

Peucedanum japonicum Thunb. dry powder was immersed in 70% ethanol and stirred overnight at room temperature. The filtrate was concentrated under reduced pressure and collected, and for the experiment it was dissolved in DMSO and evaluated.

Experiment 2: Action of Peucedanum japonicum Thunb. on Sirtuin-1 Expression

Evaluation by Western Blotting

Human umbilical vein endothelial cells (HUVEC) (LONZA, MD) were seeded in a 6-well Collagen-Coated Microplate and cultured to subconfluence. They were then incubated for 48 hours in culture medium (EBM2) containing Peucedanum japonicum Thunb. extract (final concentration: 10 µg/mL) and resveratrol (5 µM), the protein was collected with Phospho Safe Extraction Reagent (EMD chemicals, CA), and the protein concentration was measured using a BCA kit (Pierce Biotechnology, Rockford, Ill.). The sample was prepared to an equivalent protein concentration, and evaluation was conducted by Western blotting using anti-sirtuin-1 (Santa Cruz Biotechnology, CA) and anti-β-actin (Sigma Aldrich, St. Louis, Mo.) as primary antibodies and anti-rabbit (GE Healthcare, Buckinghamshire, UK) and anti-mouse (GE Healthcare, Buckinghamshire and UK) as the respective secondary antibodies. Student's t-test was used as the statistical significance test.

The results are shown in FIG. 1. With incubation after addition of Peucedanum japonicum Thunb. extract (10 µg/mL), sirtuin-1 expression was increased ($p<0.05$) compared to the control or incubation with addition of resveratrol (5 µM) as a known sirtuin-1 activating agent.

Peucedanum japonicum Thunb. is known to contain chlorogenic acid, rutin and hesperidin, but it has been reported that chlorogenic acid has no sirtuin-1 activating effect (PLoS One, 2014, 9(2), e89166), while in the case of rutin, quercetin that is produced by conversion from rutin in the body has been reported to have a sirtuin-1 expression inhibiting effect (J. Pharmacol. Sci., 2008, 108, 364-71). On the other hand, hesperidin which is found in trace amounts in Peucedanum japonicum Thunb. plant body has been reported to have an effect of activating sirtuin-1 at 5 µM (Biosci. Biotechnol. Biochem., 2012, 76(4), 640-645). However, HPLC measurement of the powder used to prepare the test sample extract revealed a hesperidin content of 0.62 wt %. Since the concentration of hesperidin (molecular weight: 610) in the extract at an effective concentration (10 µg/mL extract) is no more than 0.102 µM at maximum, the excellent sirtuin-1 activating action of Peucedanum japonicum Thunb. cannot be explained by known components.

Experiment 3. Cell Senescence-Inhibiting Effect Against Oxidative Stress

The cell senescence-inhibiting effect of Peucedanum japonicum Thunb. against oxidative stress induced by addition of $H_2O_2$ was evaluated in terms of increased activity of the senescence marker SA β-Gal (Senescence-associated β-galactosidase). Cells that have undergone cell senescence have increased SA β-Gal activity and are stained blue upon addition of substrate.

HUVEC were cultured to subconfluence in culture medium (EBM2) (Lonza, Basal, Switzerland) in a 100 mm/Collagen-Coated Dish. Next, $H_2O_2$ (final concentrations: 0 and 100 μM) was added, the mixture was incubated for 1 hour (37° C., 0.5% $CO_2$), and culture medium (EBM2) containing *Peucedanum japonicum* Thunb. extract (final concentration: 10 μg/mL) was used for reseeding to $5 \times 10^4$ cells/dish. Culturing was then carried out for 5 days, and a Cellular Senescence Assay Kit (Millipore, MA) was used for evaluation. Student's t-test was used as the statistical significance test.

The results are shown in FIG. 2. Cells incubated with culture medium containing no *Peucedanum japonicum* Thunb. extract had increased SA β-Gal activity, with blue staining of the cells, after addition of $H_2O_2$. In contrast, the cells incubated in culture medium containing *Peucedanum japonicum* Thunb. extract (10 μg/mL) had reduced blue staining (p<0.05). This indicates that SA β-Gal activity was suppressed, and thus cell senescence was suppressed, by *Peucedanum japonicum* Thunb. extract.

What is claimed is:

1. A method for activating sirtuin-1 comprising topically administrating to a subject in need of activation of sirtuin-1 a dosage form containing an effective amount of a *Peucedanum japonicum* Thunb. plant body or solvent extract thereof.

2. The method according to claim 1, wherein the solvent extract is a water-containing ethanol extract.

3. The method according to claim 1, wherein the plant body of *Peucedanum japonicum* Thunb. is the leaves, stem or entire plant.

4. A method for suppressing cell senescence due to oxidative stress comprising topically administrating to a subject in need of activation of sirtuin-1 a formulation comprising an effective amount of a *Peucedanum japonicum* Thunb. plant body or solvent extract thereof, wherein the cell senescence due to oxidative stress is suppressed via activation of sirtuin-1 in the subject.

5. The method according to claim 4, wherein the solvent extract is a water-containing ethanol extract.

6. The method according to claim 4, wherein the plant body of *Peucedanum japonicum* Thunb. is the leaves, stem or entire plant.

* * * * *